(12) United States Patent
Weston et al.

(10) Patent No.: US 6,258,059 B1
(45) Date of Patent: Jul. 10, 2001

(54) INJECTION AID

(75) Inventors: Terence Edward Weston, Eye; Douglas Arthur Emmott, Ipswich, both of (GB)

(73) Assignee: Weston Medical Limited, Eye (GB)

( * ) Notice: Subject to any disclaimer, the term of this patent is extended or adjusted under 35 U.S.C. 154(b) by 0 days.

(21) Appl. No.: 09/599,653

(22) Filed: Jun. 21, 2000

Related U.S. Application Data

(63) Continuation of application No. 09/117,952, filed on Aug. 7, 1998, which is a continuation of application No. PCT/GB97/00351, filed on Feb. 6, 1997.

(51) Int. Cl.$^7$ .................................................... A61M 5/00
(52) U.S. Cl. ............................................................ 604/116
(58) Field of Search ................................ 604/116, 68, 71, 604/72, 131, 137, 307

(56) References Cited

U.S. PATENT DOCUMENTS

| | | |
|---|---|---|
| 3,058,466 | 10/1962 | Routsong . |
| 3,760,803 | 9/1973 | Boothby . |
| 3,934,590 | 1/1976 | Campagna et al. . |
| 4,085,750 | 4/1978 | Bosshold . |
| 4,150,669 | 4/1979 | Latorre . |
| 5,064,420 | 11/1991 | Clarke et al. . |
| 5,147,306 | 9/1992 | Gubich . |
| 5,154,710 | 10/1992 | Williams . |
| 5,207,659 | 5/1993 | Pennaneac'h et al. . |
| 5,221,027 | 6/1993 | Gibilsco . |
| 5,312,335 | 5/1994 | McKinnon et al. . |
| 5,352,211 | 10/1994 | Merskelly . |
| 5,368,023 | 11/1994 | Wolf . |
| 5,836,911 | 11/1998 | Marzynski et al. . |

FOREIGN PATENT DOCUMENTS

| | | |
|---|---|---|
| 2 699 083 A1 | 6/1994 | (FR) . |
| WO 97/27834 | 8/1997 | (WO) . |

*Primary Examiner*—Manuel Mendez
(74) *Attorney, Agent, or Firm*—Darby & Darby

(57) ABSTRACT

An injection aid is provided for use in injecting material through the skin of a recipient at a precisely defined point. The injection aid has a boss or the like which receives the outlet end of the injector. The injection aid is maintained at the desired location on the skin. In one embodiment, designed for use in treating erectile dysfunction, this is achieved by a C-shaped ring, and in another embodiment this is achieved by an adhesive-coated flange.

6 Claims, 4 Drawing Sheets

INJECTION AID

This Appln is a cont of Ser. No. 09/117,952 filed Aug. 7, 1998, which is a cont of PCT/GB97/00351 filed Feb. 6, 1997.

FIELD OF THE INVENTION

This invention relates to an injection aid which is placed on the skin of a subject to be needlelessly injected with a medicament, in order to improve the accuracy of positioning the injector. The injection aid is particularly useful when it is important to give the injection at a very precise place on the skin, such as when injecting the penis for treating erectile dysfunction, or injecting keloid scars to reduce them.

BACKGROUND OF THE INVENTION

Needleless injectors are used as an alternative to hypodermic needle syringes to deliver medicaments through the patient's skin into the underlying tissues. Instead of piercing the skin with a hollow needle, a needleless injector employs a high pressure piston pump to "fire" a fine jet of liquid medicament with sufficient force to puncture the skin, and the remaining medicament is injected through the hole thus formed.

The technique was first used commercially in the 1950's, and is particularly appealing to those who fear needles—so called needlephobia. More recently there has been a surge of interest in needleless injection because it eliminates needle-stick injuries, eliminates cross-contamination, and is potentially superior for self administered injections.

One application for needleless injectors is the treatment of erectile dysfunction. Not surprisingly, men suffer a high incidence of needlephobia, since the normal treatment is to inject the medicament with a 12 mm long needle directly into the corpus cavernosum. There have been attempts recently to inject with a needleless injector, but injectors currently available require considerable skill to operate, and the placement requirements for the injector are critical. It is important that the injection misses any superficial blood vessels, and the force of the nozzle on the skin must not be too high, as this would compress the tissues to an undesirable extent and possibly cause the jet of medicament to pass through the corpus cavernosum. Equally, the force of the nozzle on the skin must not be too light or non-existent, since this could result in wasted injectate, bruising or tearing of the skin, haematomas, and poor therapeutic effect. Most currently available needleless injectors are fairly large—typically 160 mm long by 18 mm diameter, and the delivery orifice in the nozzle is difficult to place with the required accuracy, because the surrounding structure obscures the injection site. Most injectors are operated by pressing the nozzle onto the skin and actuating a release button which is usually placed on the opposite end of the injector to the nozzle: at the instant of pressing the injection release button there is invariably a reaction jerk of the injector body which can shift the position of the nozzle at the instant of injection. Furthermore, there is no means provided to ensure that optimum nozzle to skin force is achieved before operating the injector, and variable results are obtained. The present inventor has co-pending applications (e.g. PCT/GB94/01608) in which many of these problems are avoided by arranging for the injector to be triggered in response to a predetermined force of the nozzle on the skin. Nevertheless, with some applications such as the treatment of erectile dysfunction, the injection site is extraordinarily soft and motile, requiring precise positioning, and further skill and care is required.

Another application for needleless injectors is the treatment of keloids—or raised scar tissue. In this case a number of injections are made over the area of the keloid, and it is important to position these carefully. Again, no devices are known to the present inventor which help to improve the positioning accuracy.

SUMMARY OF THE INVENTION

The present invention seeks to improve the positioning accuracy of needleless injectors by providing a location boss which, in use, is first placed on the skin at the required injection site, and which cooperates with the injection nozzle of the injector when placed therein.

In a preferred embodiment, specifically for treating erectile dysfunction, a partial ring in the shape of a "C" of flat, flexible, resilient material is provided with a finger grip, otherwise referred to herein as a lug, on each open end, and approximately diametrically opposite the gap between the finger grips, there is provided a raised hollow boss, which is preferably integral with the "C". A small hole concentrically disposed within the boss extends through the flat material of the ring. To use the device, it is placed over the penis with the small hole at the desired injection site, and the lugs are squeezed together between thumb and forefinger so as to lightly compress the penis and prevent slippage of the device. The boss is dimensioned to locate the nozzle of the injector so that the orifice of the nozzle touches the skin, and the injector is placed within the boss and pressed towards the penis. The injector is supported by the ring, and moderate variations in the pressing force will not cause the penis to be squashed. The injector is then operated to cause the injection.

In a second preferred embodiment, there is provided a location boss as previously described, which is surrounded by a flange, which may be flexible. The flange has an adhesive on one face by which means it may be positioned at the injection site and temporarily retained. The adhesive may have a peelable backing to protect it during storage.

In both preferred embodiments, a small hole is used to center the device at the desired injection site: the vernier acuity of the eye is very good, and placement within one millimeter of the desired injection site is accomplished with ease.

BRIEF DESCRIPTION OF THE DRAWINGS

The invention will now be further described with reference to the accompanying drawings, in which.

DETAILED DESCRIPTION OF THE INVENTION

Figure 1A:
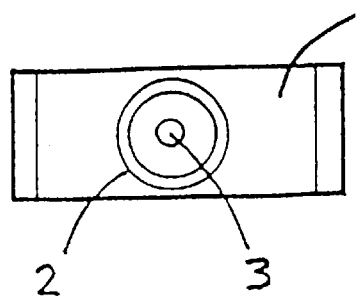
FIGS. 1a, 1b, 1c show a ring-shaped injection aid, FIG. 1b being a projection of FIG. 1a, and FIG. 1c being an enlarged cross-section of the location boss with an injector nozzle therein.
Figure 1B:
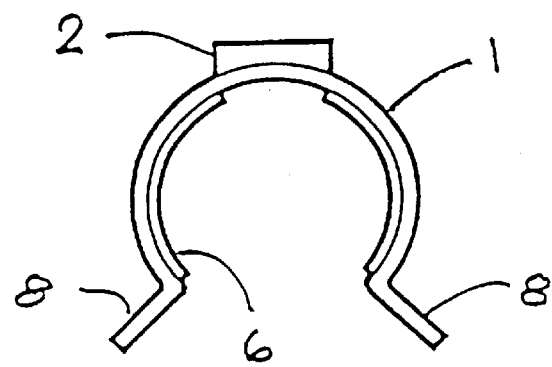
Figure 1C:
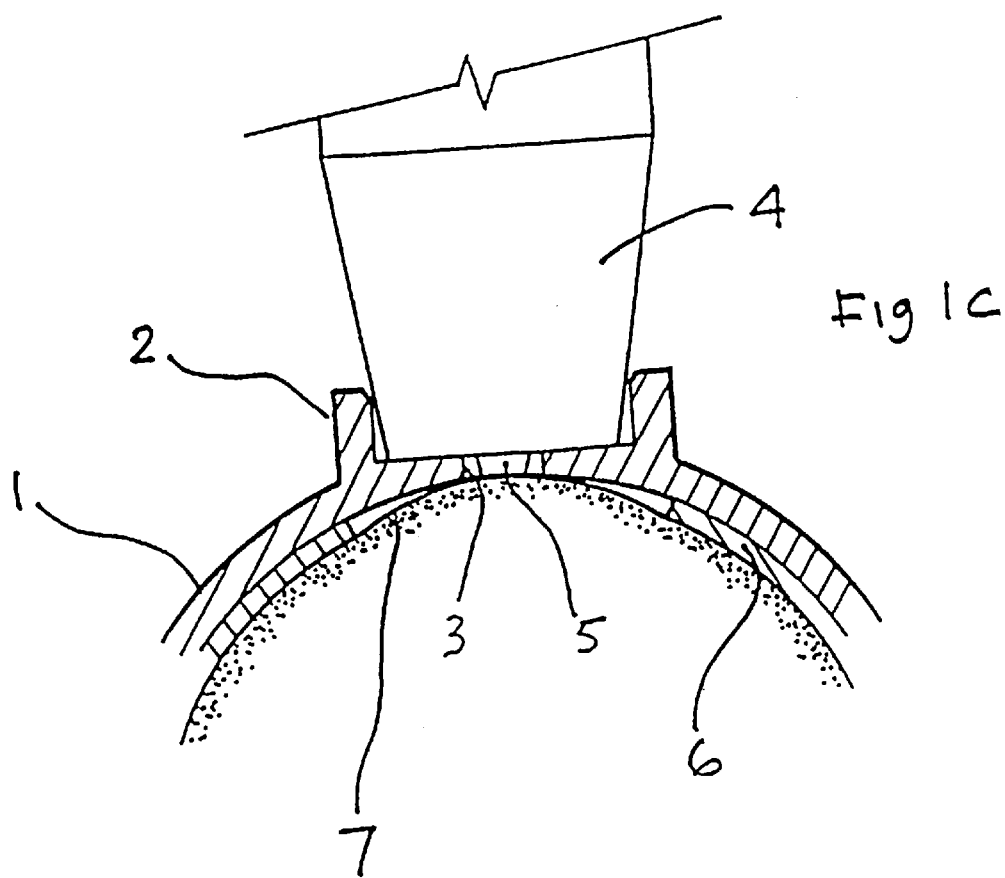
Figure 2:
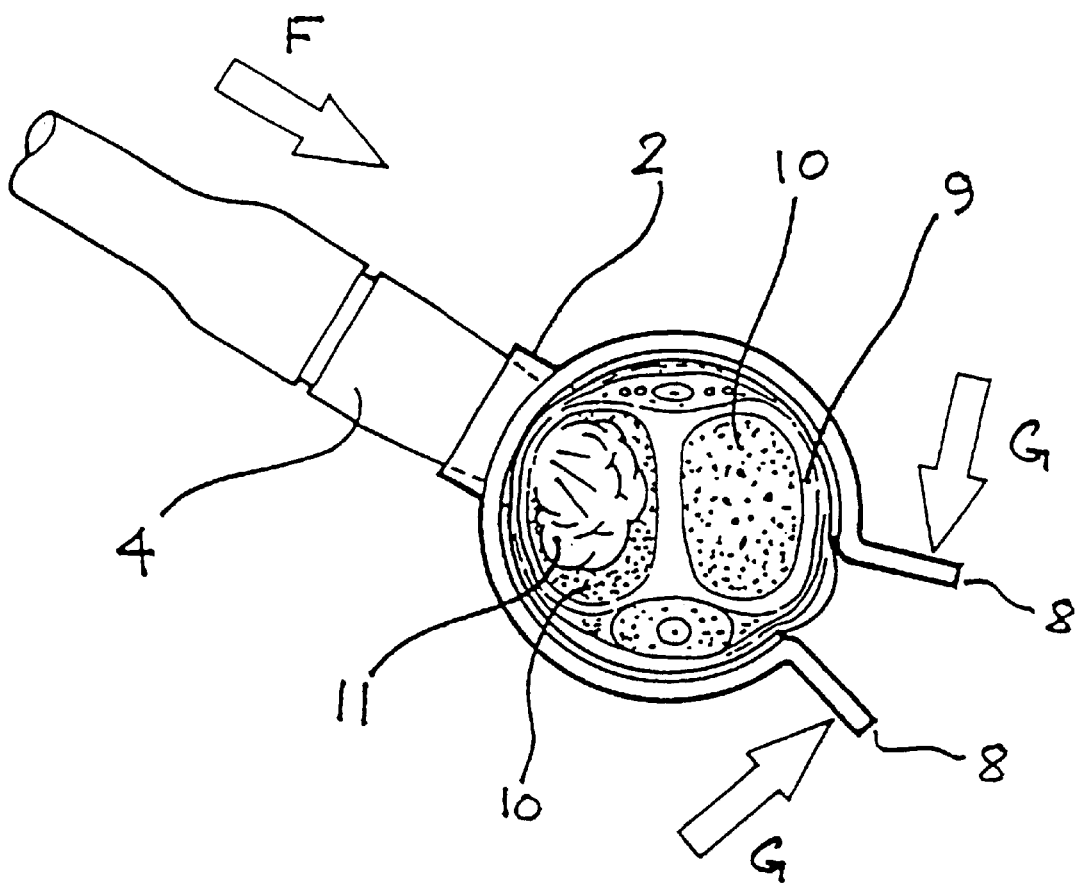
FIG. 2 is a cross-section of a penis with the ring-shaped injection aid in place.
Figure 3:
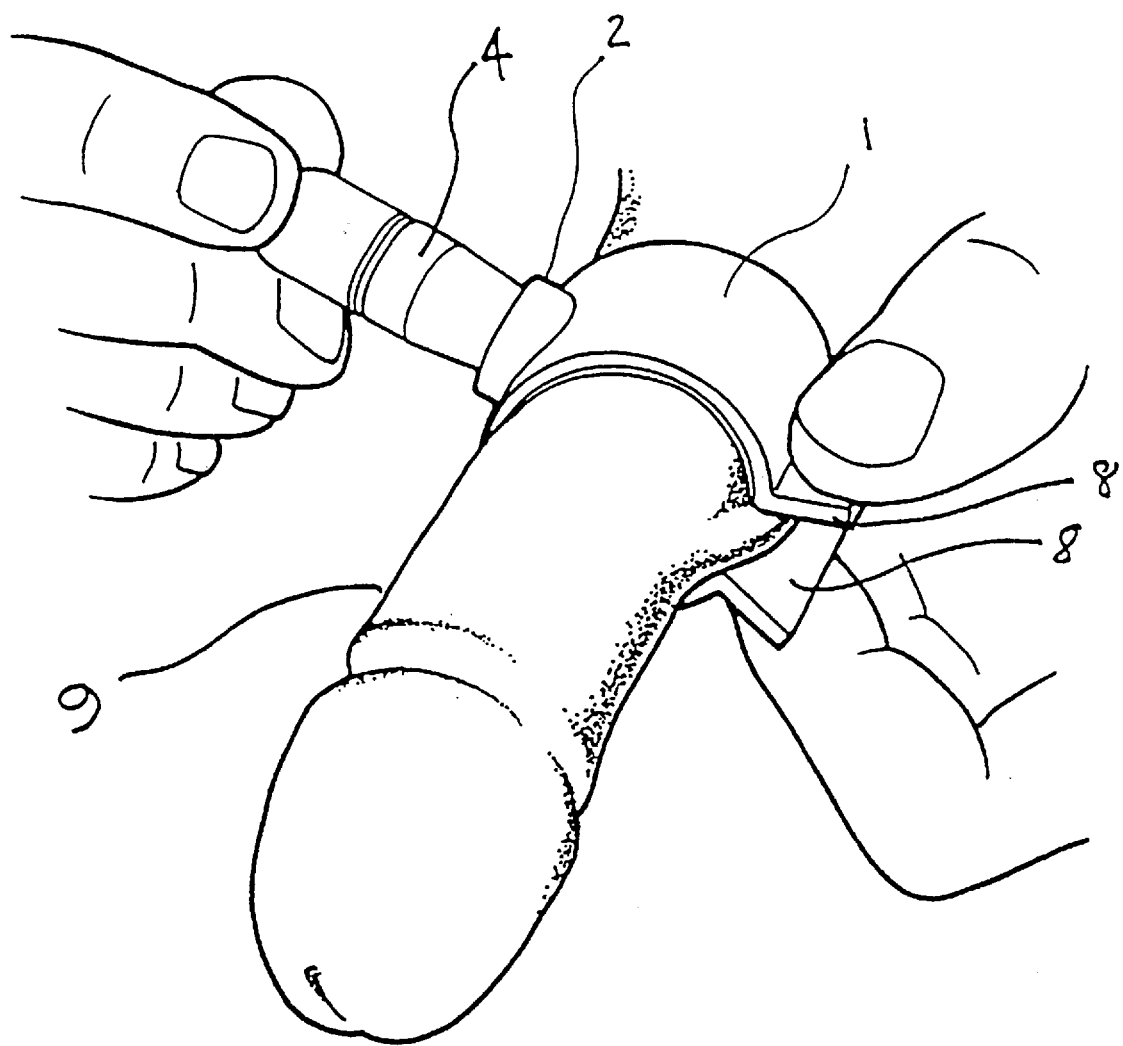
FIG. 3 is a general view of the injection aid of the preceding Figures in use.

Referring to FIGS. 1a and 1b, a flexible, resilient, "C"-shaped ring 1 of flat material is provided with finger lugs 8 at each open end. A circular hollow boss 2 is mounted on the ring 1 approximately opposite the gap between the two lugs. In the center of the boss 2 is a hole 3, which extends through the ring 1 and may be about 5 mm diameter. FIG. 1*c* is a part cross-section through the hollow boss 2, with a needleless injector 4 located therein so that its nozzle 5 touches the skin 7 of the penis. A thin soft insulating layer 6 may be bonded to the inside of the "C"-shaped ring 1 for comfort. FIG. 2 is a cross-section through the penis 9, with the injection aid applied and injector 4 located within the boss 2. A force G is applied by hand to the lugs 8 to gently compress the penis, and a force F on the injector 4 is resisted by the injection aid being supported by the hand holding the lugs 8. This is illustrated fully in FIG. 3.

Figure 4A:
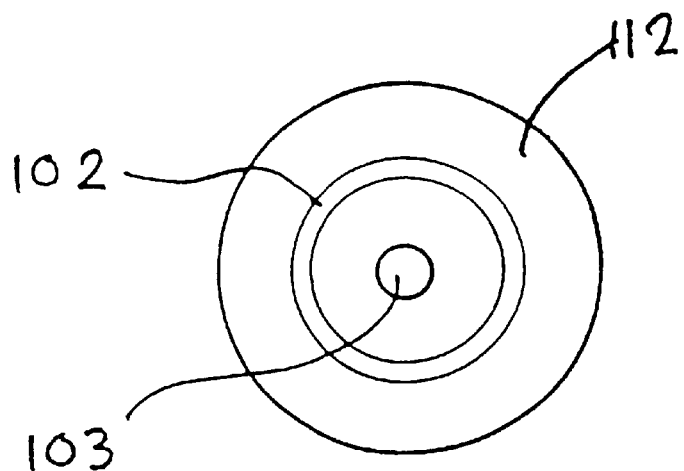
FIGS. 4a, 4b, 4c are views of an adhesive-backed injection aid.
Figure 4B:
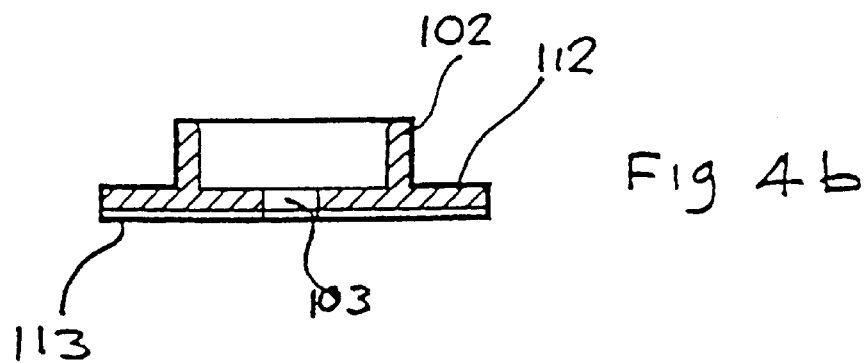
Figure 4C:
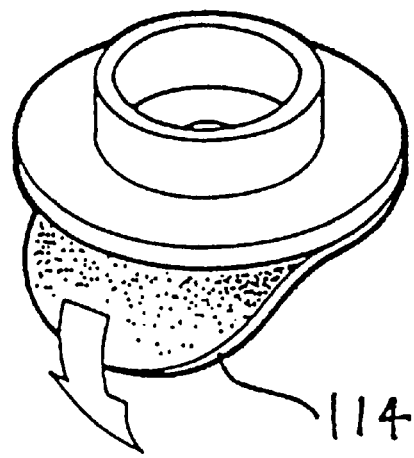

FIGS. 4*a*, 4*b* and 4*c* are views of an injection aid 101 for more general use. A hollow boss 102 and small hole 103 are integral with a flange 112. Flange 112 may be flexible and there may be radial slots therein (not shown) to increase the flexibility. On the underside of the flange 112 is an adhesive layer 113 which also may be insulating for comfort. The adhesive layer may have a peelable protective film 114 as shown in FIG. 4*c*. To use the device, the film 14 is peeled away from the adhesive, the hole 103 placed over the desired injection site, and the flange 112 pressed onto the skin to retain the device temporarily. The injector is then placed within the hollow boss 102 and the injector is then placed within the hollow boss 102 and the injection made as previously described.

In all of the foregoing examples, the precise details of the hollow boss will vary according to the injector nozzle and operating characteristics of the injector.

What is claimed is:

1. An injection aid for use in injecting material through the skin of a recipient with a needleless injector having an outlet end provided with an outlet orifice, comprising: means for receiving the outlet end, and locating means for enabling the receiving means to be maintained at a desired location on the skin during injection, the locating means including a flange extending from the receiving means and forming a continuous unobstructed contacting surface for engagement with the skin of the recipient.

2. An injection aid according to claim 1, wherein the receiving means comprises a boss surrounding a hole providing access to the recipient's skin.

3. An injection aid for use in injecting material through skin of a recipient with a needleless injector having an outlet end provided with an outlet orifice, which comprises means for receiving the outlet end, and locating means for enabling the receiving means to be maintained at a desired location on the screen during injection, wherein a flange extends naturally from the receiving means for engagement with the skin, wherein a layer of adhesive is provided on the side of the flange intended to face the skin.

4. An injection aid according to claim 3, wherein the receiving means comprises a boss surrounding a hole providing access to the recipient's skin.

5. An injection aid for use in injecting material through skin of a recipient with a needleless injector having an outlet end provided with an outlet orifice, which comprises means for receiving the outlet end, and locating means for enabling the receiving means to be maintained at a desired location on the skin during injection, wherein the locating means is provided by a layer of adhesive.

6. An injection aid according to claim 5, wherein the receiving means comprises a boss surrounding a hold providing access to the recipient's skin.

* * * * *